United States Patent [19]
Woehr et al.

[11] Patent Number: 6,117,108
[45] Date of Patent: *Sep. 12, 2000

[54] SPRING CLIP SAFETY IV CATHETER

[76] Inventors: Kevin Woehr, Danziger Strasse No. 2, Felsberg; Manfred Orth, Falkensteinstr. 63, Kassel, both of Germany; Mark Wynkoop, 3319 Lanark Rd., Coopersberg, Pa. 18036; Matthew Kohler, 4097 E. Mill Hill Rd., E. Greenville, Pa. 18041

[*] Notice: This patent issued on a continued prosecution application filed under 37 CFR 1.53(d), and is subject to the twenty year patent term provisions of 35 U.S.C. 154(a)(2).

[21] Appl. No.: 09/097,170

[22] Filed: Jun. 12, 1998

Related U.S. Application Data

[63] Continuation-in-part of application No. 08/915,148, Aug. 20, 1997, abandoned.

[51] Int. Cl.[7] ........................................... A61M 5/00
[52] U.S. Cl. ............................... 604/110; 604/263
[58] Field of Search ..................... 604/110, 263

[56] References Cited

U.S. PATENT DOCUMENTS

| | | |
|---|---|---|
| 3,610,240 | 10/1971 | Harautuneian . |
| 3,904,033 | 9/1975 | Haerr . |
| 4,160,450 | 7/1979 | Doherty . |
| 4,725,267 | 2/1988 | Vaillancourt . |
| 4,735,618 | 4/1988 | Hagen . |
| 4,747,831 | 5/1988 | Kulli . |
| 4,795,432 | 1/1989 | Karczmer . |
| 4,846,809 | 7/1989 | Sims . |
| 4,929,241 | 5/1990 | Kulli ........................ 604/263 |
| 4,944,725 | 7/1990 | McDonald . |
| 4,952,207 | 8/1990 | Lemieux . |
| 4,964,854 | 10/1990 | Luther . |
| 4,978,344 | 12/1990 | Dombrowski et al. . |
| 4,994,041 | 2/1991 | Dombrowski et al. . |
| 5,049,136 | 9/1991 | Johnson . |
| 5,051,109 | 9/1991 | Simon . |
| 5,053,017 | 10/1991 | Chamuel ..................... 604/192 |
| 5,085,648 | 2/1992 | Purdy et al. . |
| 5,126,090 | 6/1992 | Egolf et al. . |
| 5,135,504 | 8/1992 | McLees ..................... 604/164 |
| 5,147,327 | 9/1992 | Johnson . |
| 5,171,229 | 12/1992 | McNeil et al. . |
| 5,183,468 | 2/1993 | McLees . |
| 5,215,528 | 6/1993 | Purdy et al. . |
| 5,279,591 | 1/1994 | Simon ....................... 604/263 |
| 5,300,045 | 4/1994 | Plassche, Jr. ............... 604/263 |
| 5,322,517 | 6/1994 | Sircom et al. . |
| 5,328,482 | 7/1994 | Sircom et al. . |
| 5,334,158 | 8/1994 | McLees . |
| 5,344,408 | 9/1994 | Partika ....................... 604/192 |
| 5,370,623 | 12/1994 | Kreamer . |
| 5,423,766 | 6/1995 | Di Cesare . |
| 5,501,675 | 3/1996 | Erskine . |
| 5,558,651 | 9/1996 | Crawford et al. . |
| 5,584,809 | 12/1996 | Gaba . |
| 5,584,810 | 12/1996 | Brimhall . |

(List continued on next page.)

FOREIGN PATENT DOCUMENTS

WO9742989A  11/1997  WIPO .

*Primary Examiner*—Corrine McDermott
*Attorney, Agent, or Firm*—Marvin N. Gordon

[57] ABSTRACT

A safety IV catheter includes a unitary, resilient needle guard received in a catheter hub. The needle guard includes a proximal arm or wall that includes an opening through which a needle passes for axial movement. When the needle is retracted from the catheter it releases the force that had previously prevented movement of the needle guard within the catheter hub. This in turn causes the needle guard to snap into a position in which it is clamped onto the needle shaft and in which its distal wall blocks access to the needle tip. In this condition, the spring needle guard and needle can be removed from the catheter hub. A slot or bulge may be formed in the needle shaft that engages with the needle guard after the protected needle and needle guard are removed from the catheter hub, thereby to prevent removal of the protected needle from the needle guard.

25 Claims, 13 Drawing Sheets

U.S. PATENT DOCUMENTS

| | | |
|---|---|---|
| 5,584,818 | 12/1996 | Morrison . |
| 5,599,310 | 2/1997 | Bogert . |
| 5,601,536 | 2/1997 | Crawford et al. . |
| 5,611,781 | 3/1997 | Sircom et al. . |
| 5,662,610 | 9/1997 | Sircom et al. . |
| 5,697,907 | 12/1997 | Gaba . |
| 5,718,688 | 2/1998 | Wozencroft . |
| 5,738,665 | 4/1998 | Caizza et al. . |
| 5,910,130 | 6/1999 | Caizza et al. ............... 604/110 |
| 5,925,020 | 7/1999 | Nestell ....................... 604/198 |
| 6,004,294 | 12/1999 | Brimhall et al. ............ 604/164 |

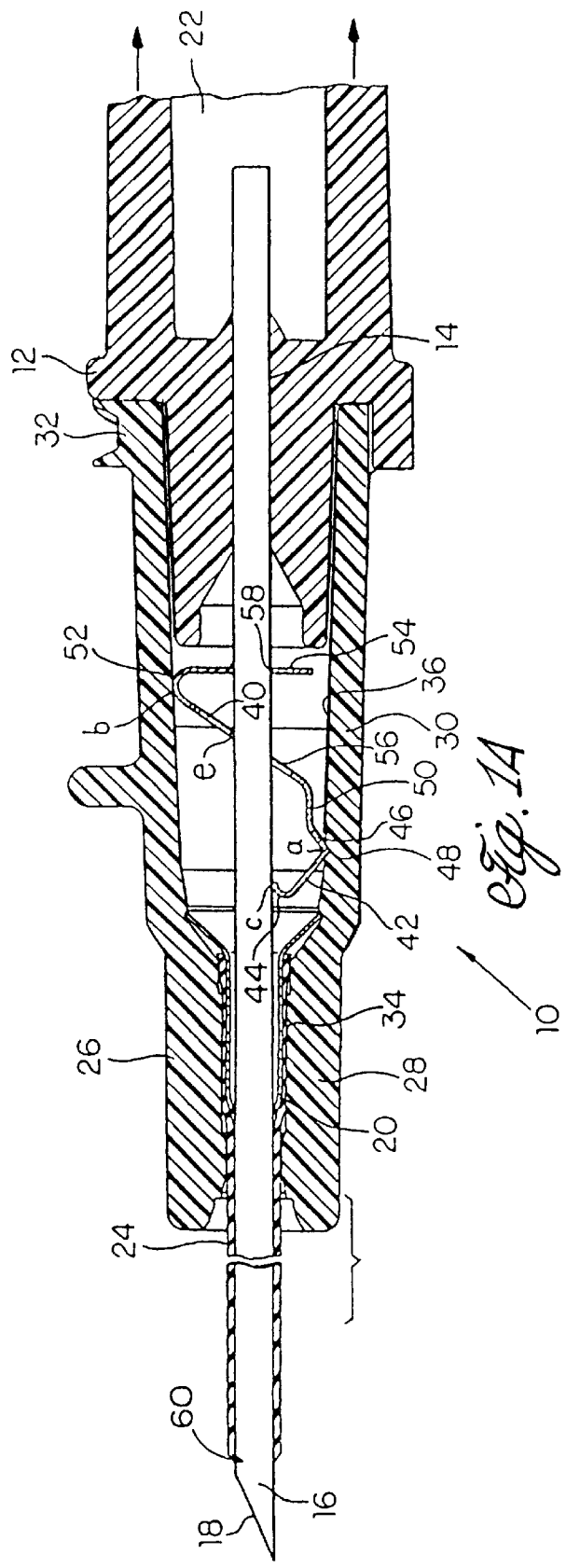
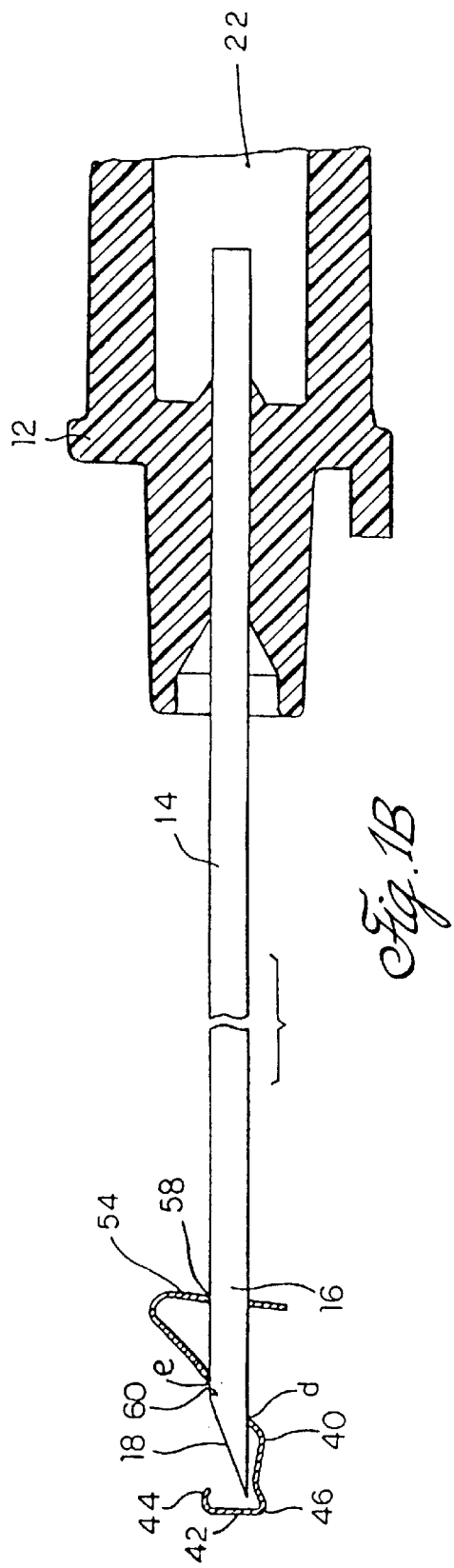
Fig. 1A
Fig. 1B

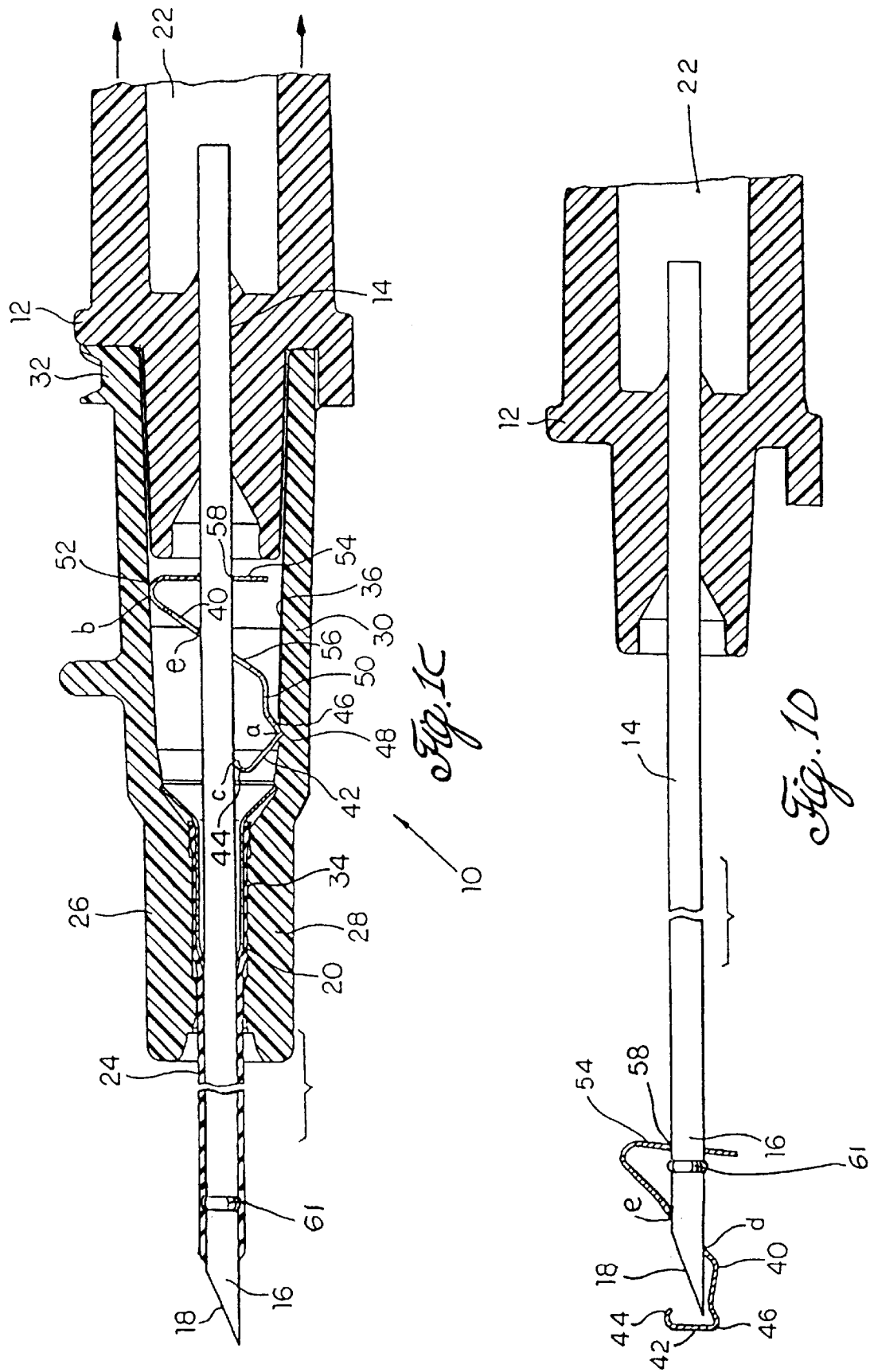

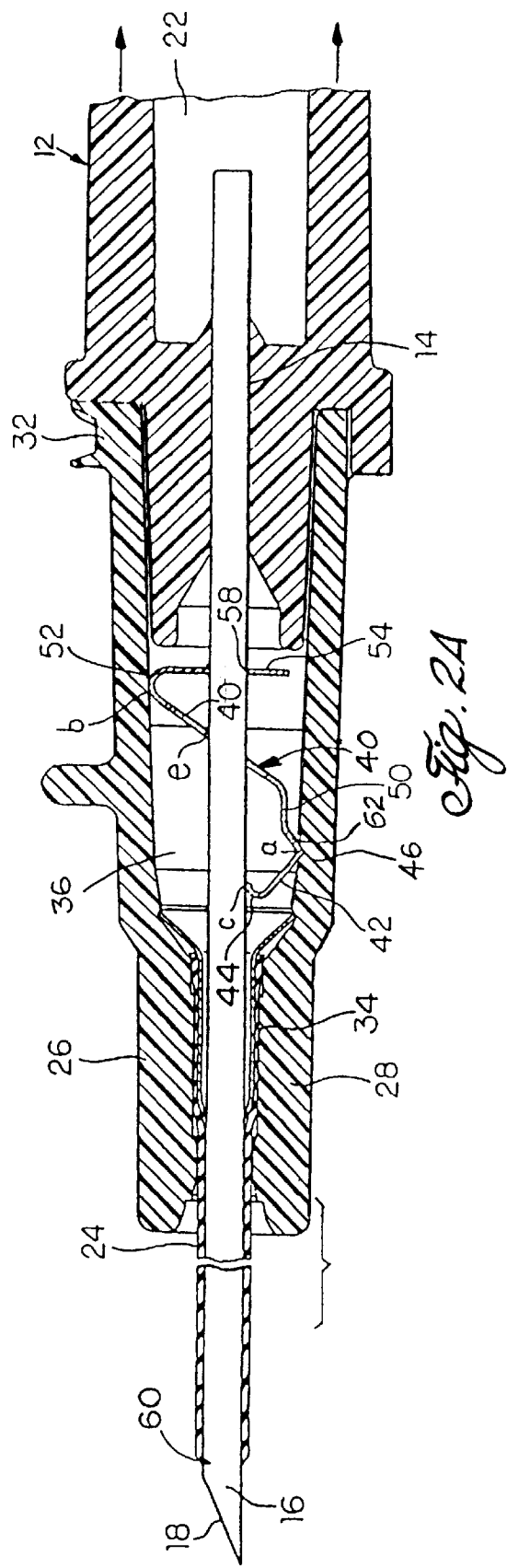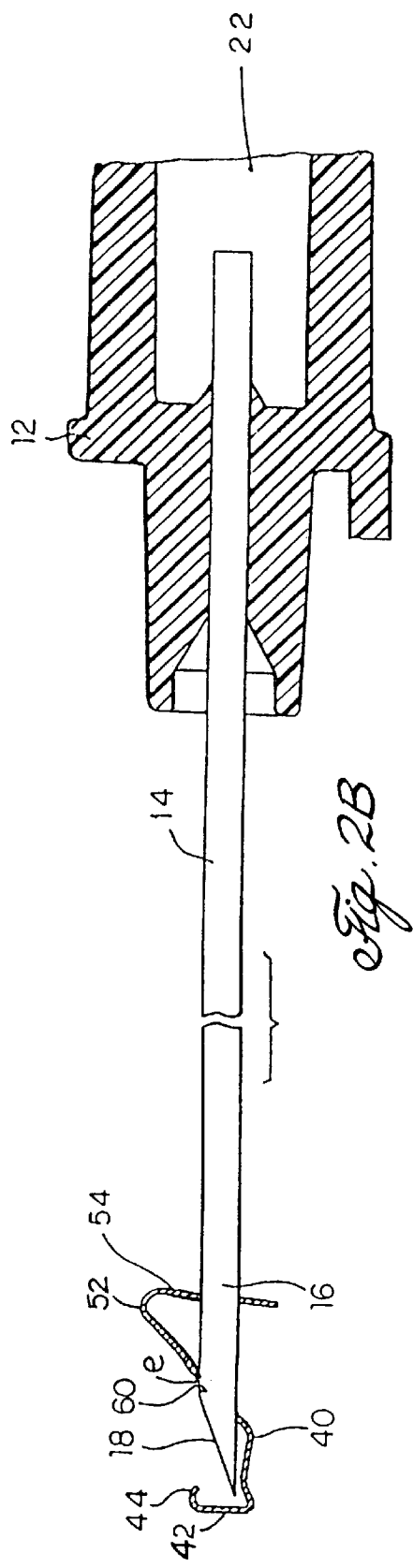

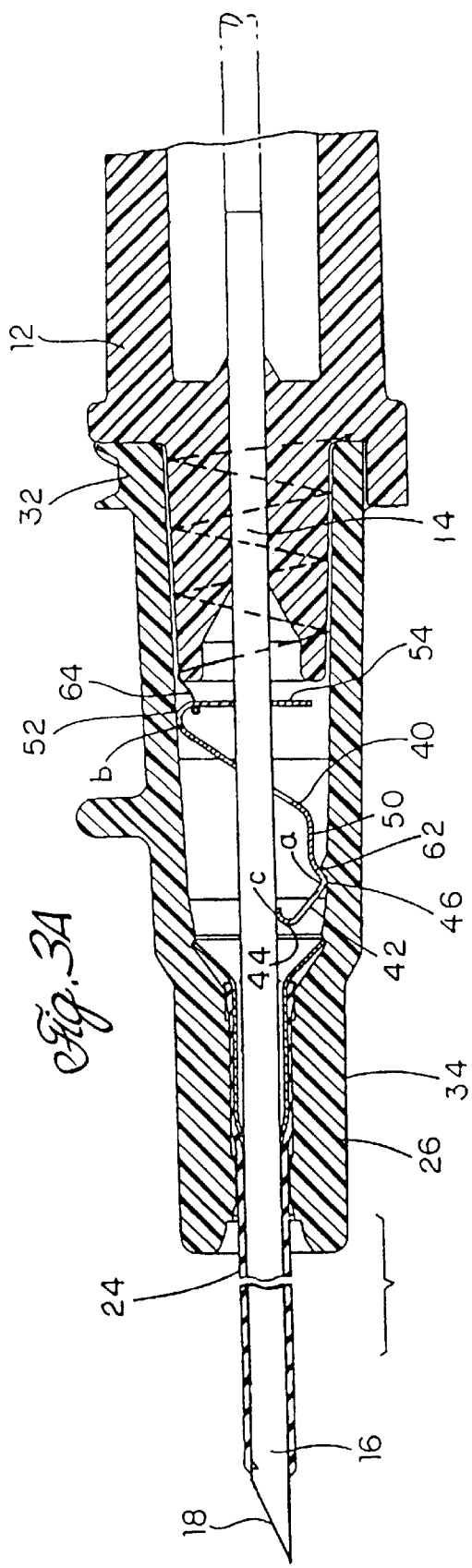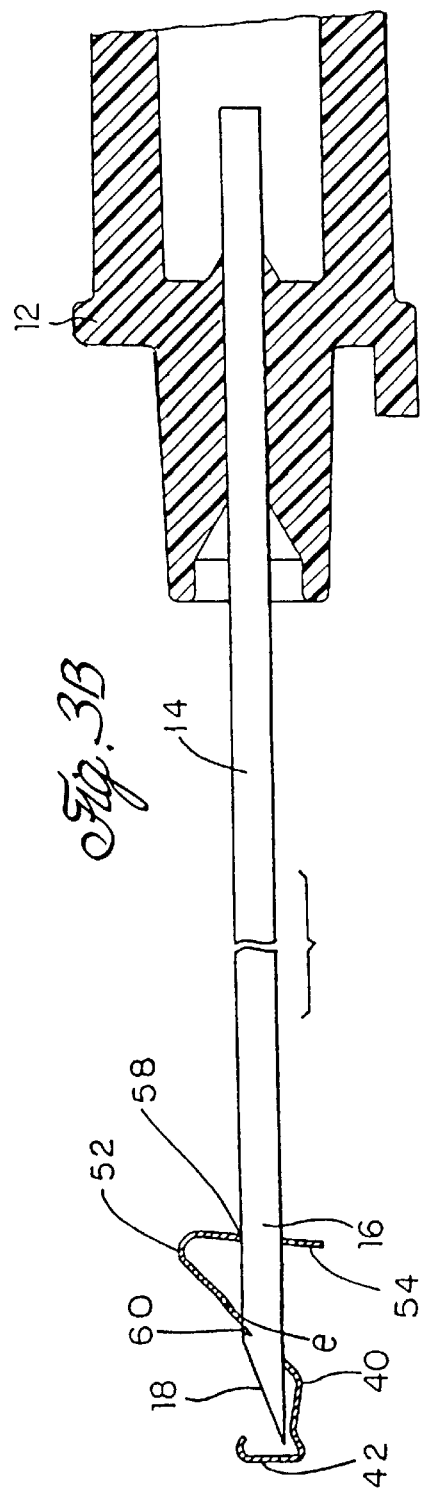

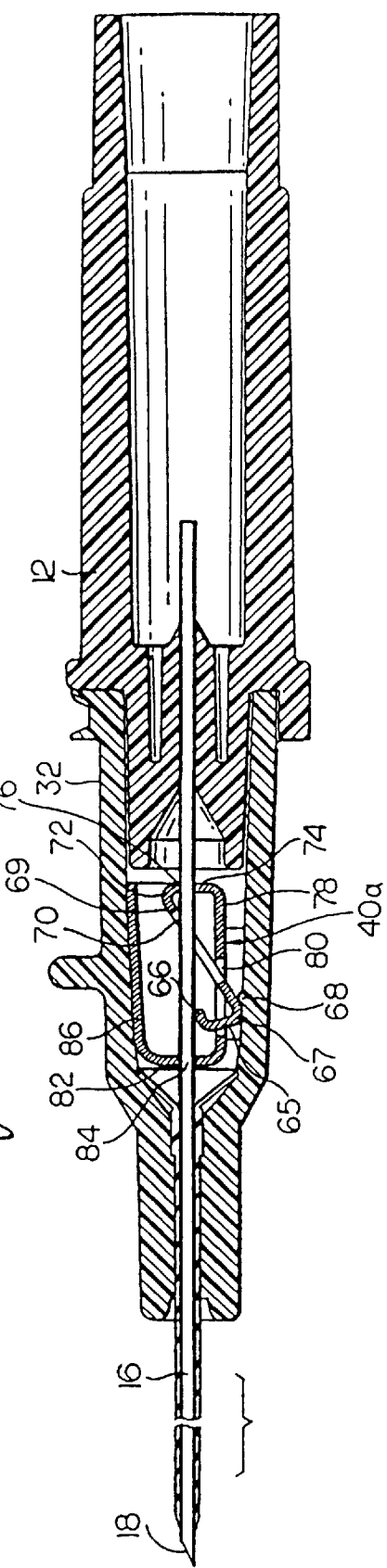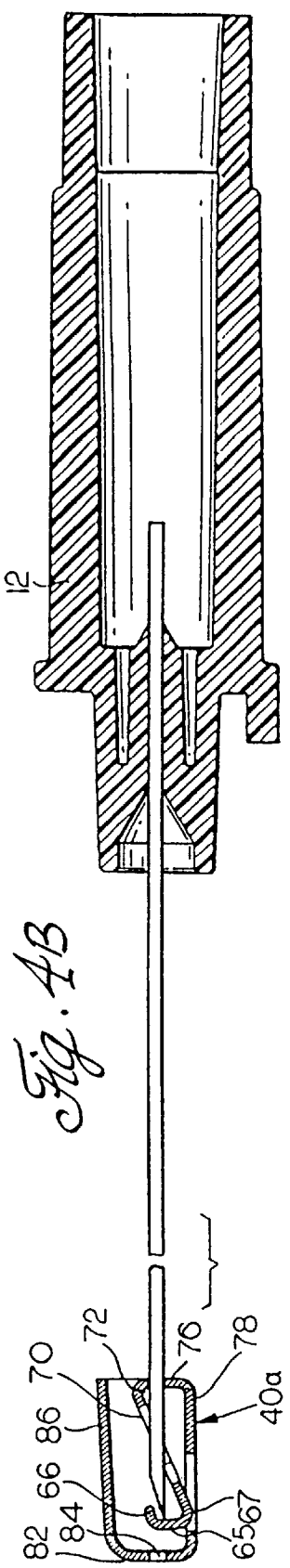

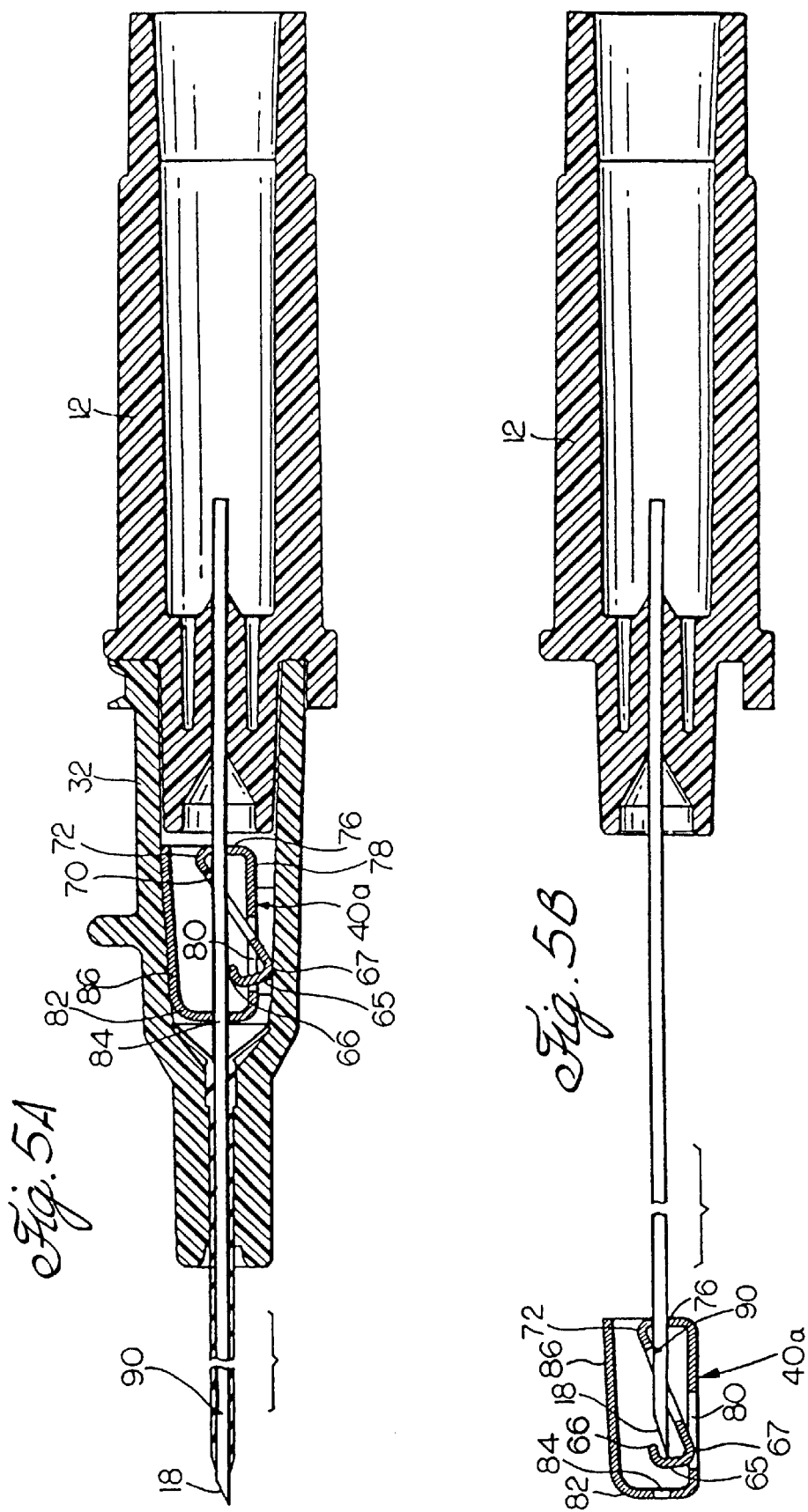

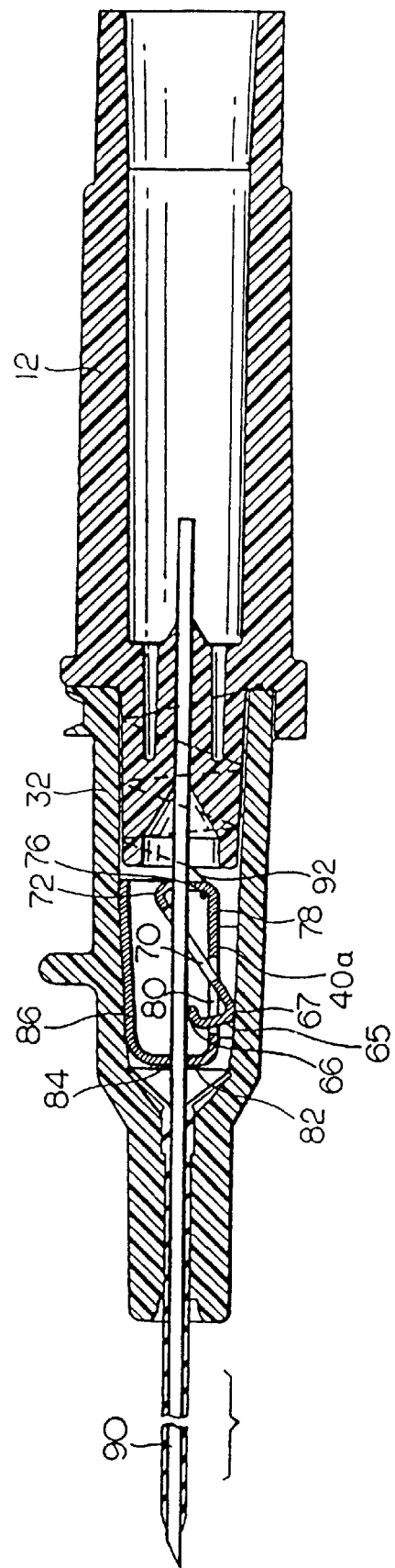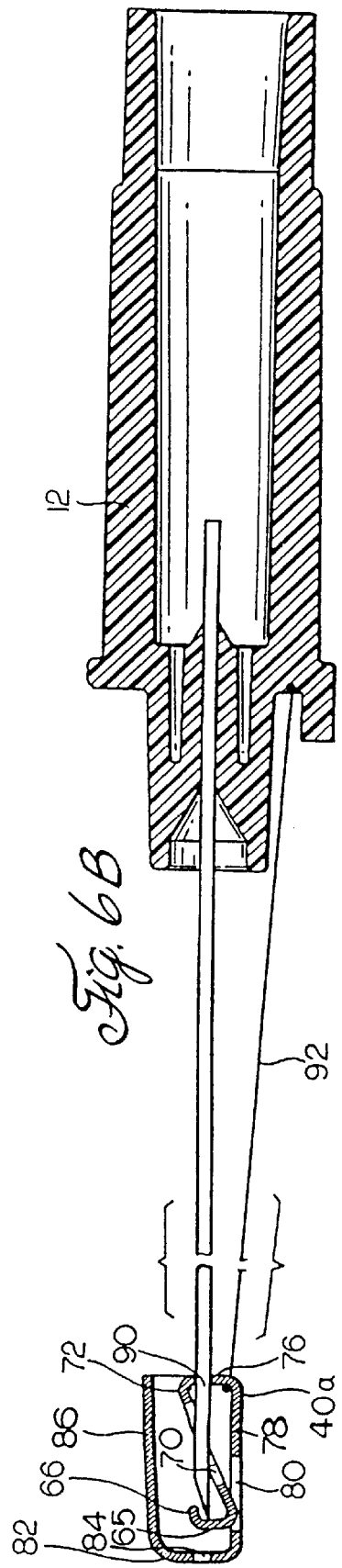

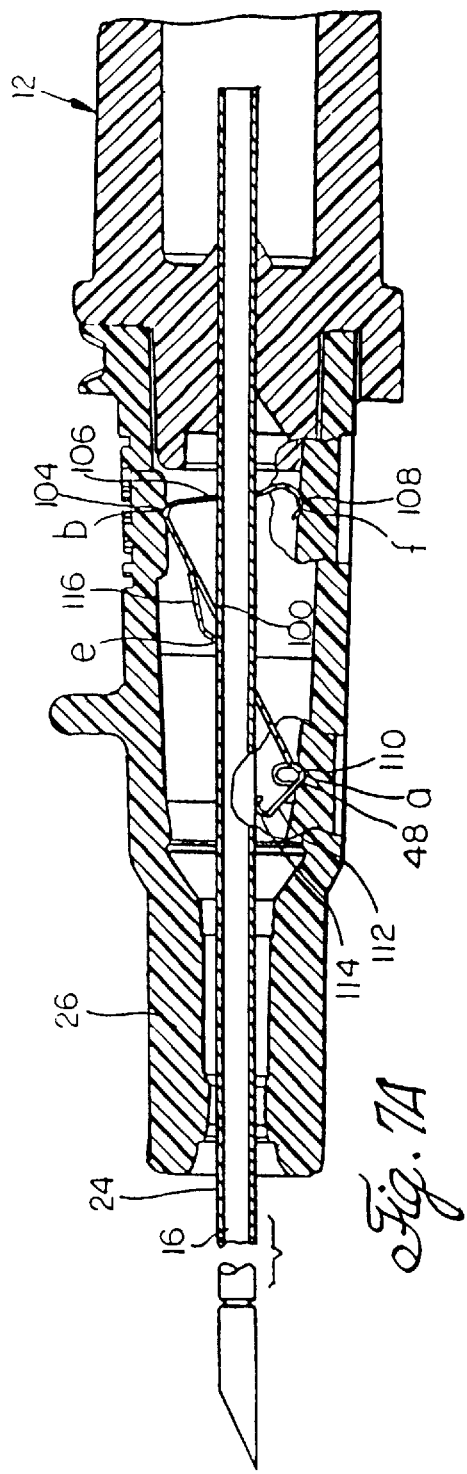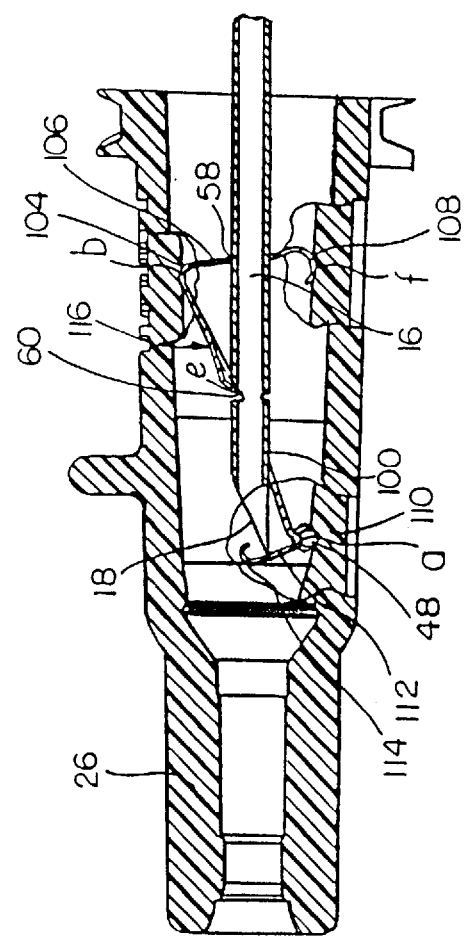

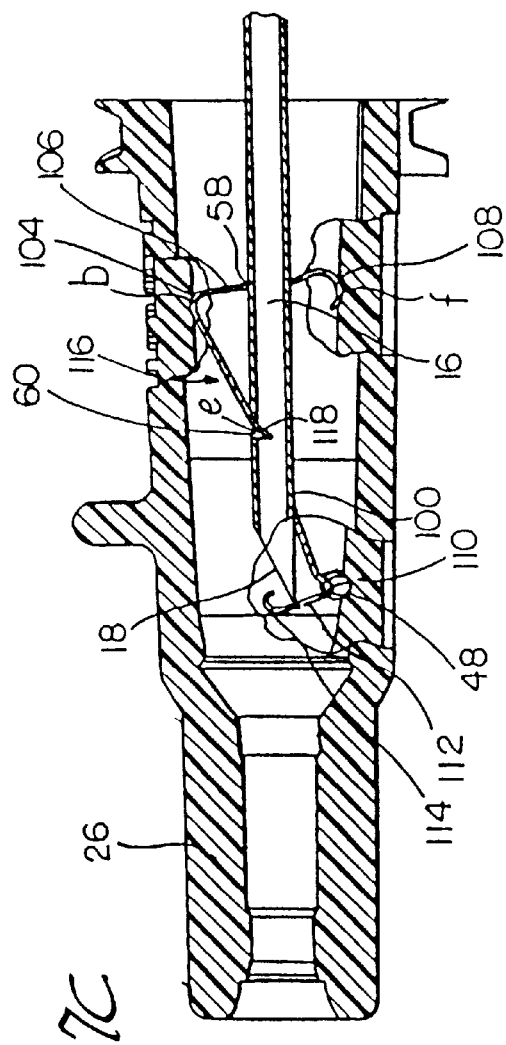
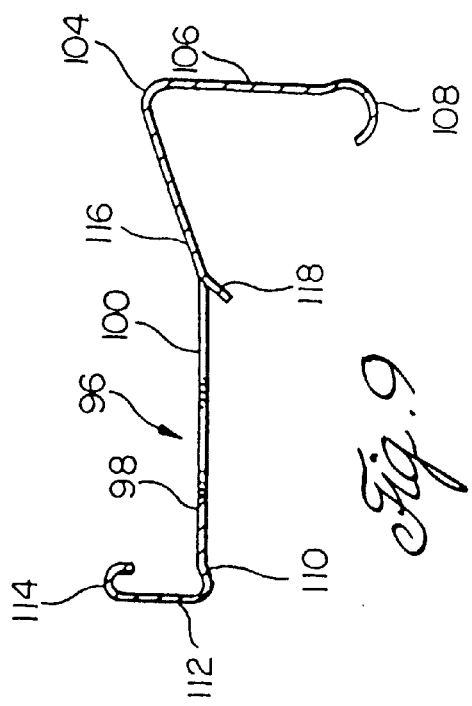
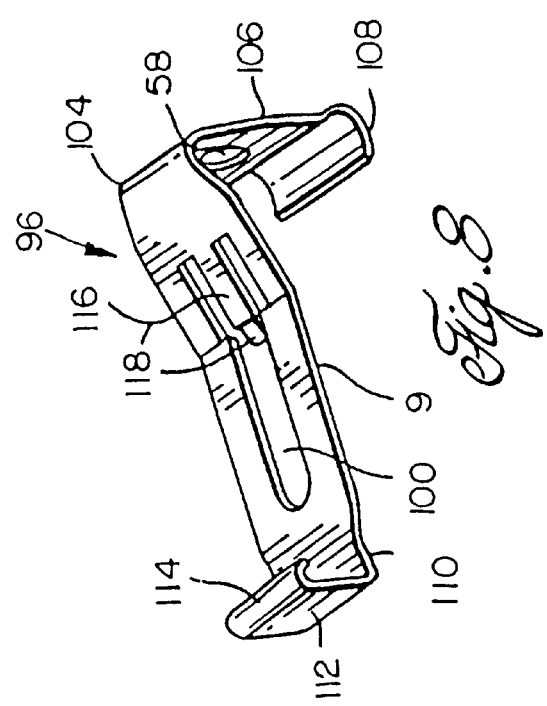

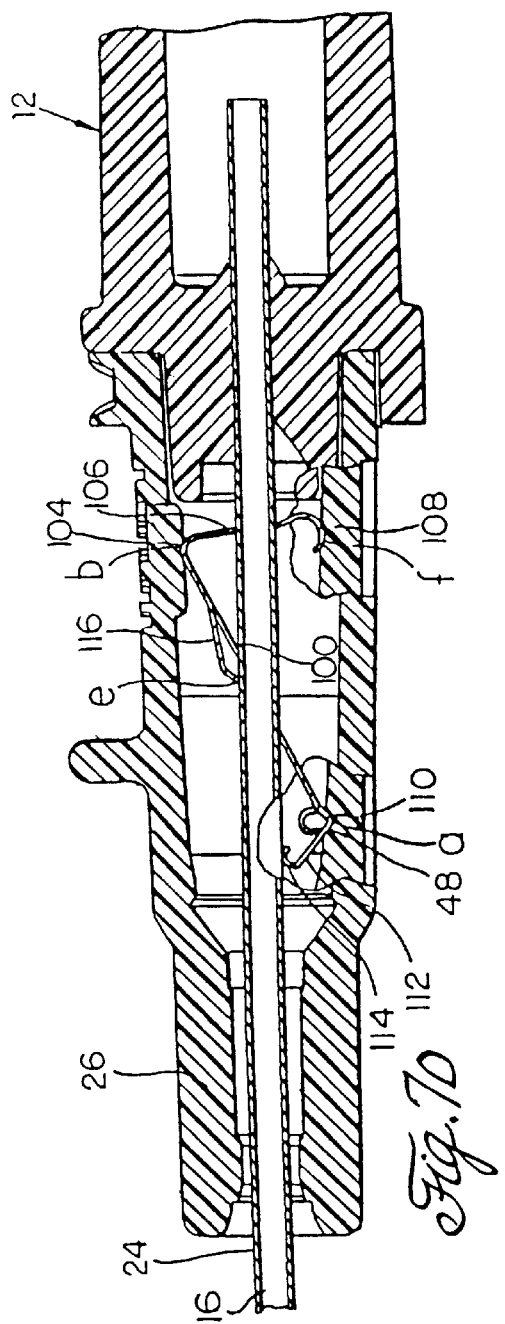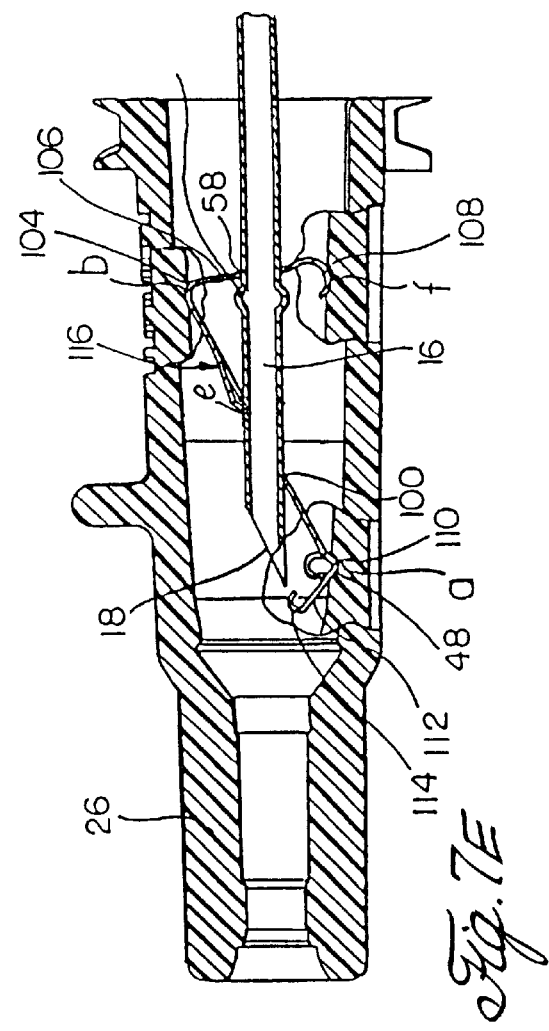

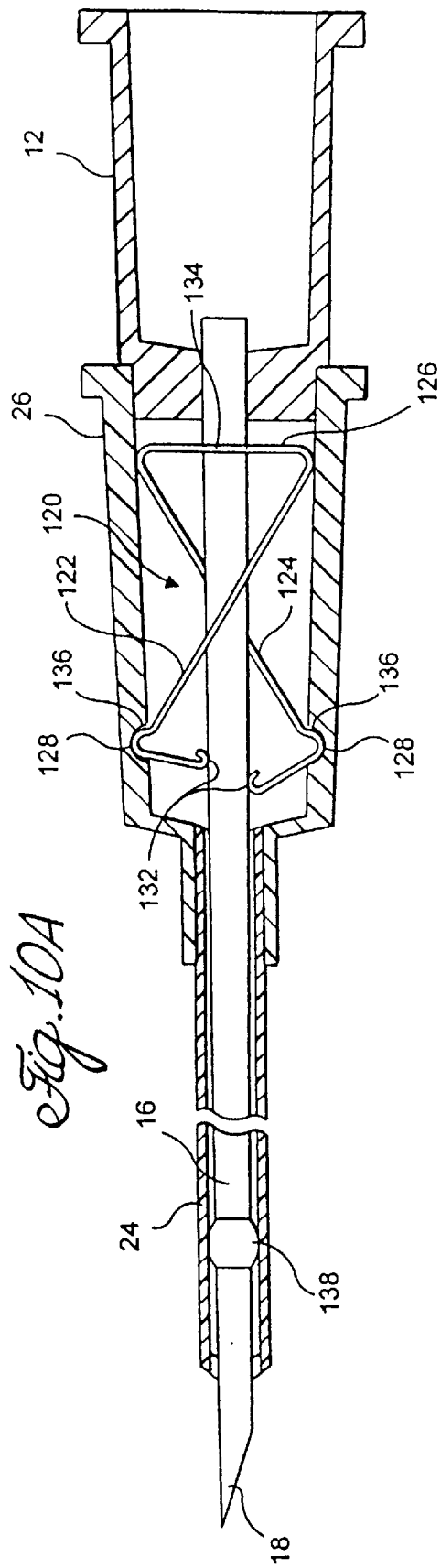
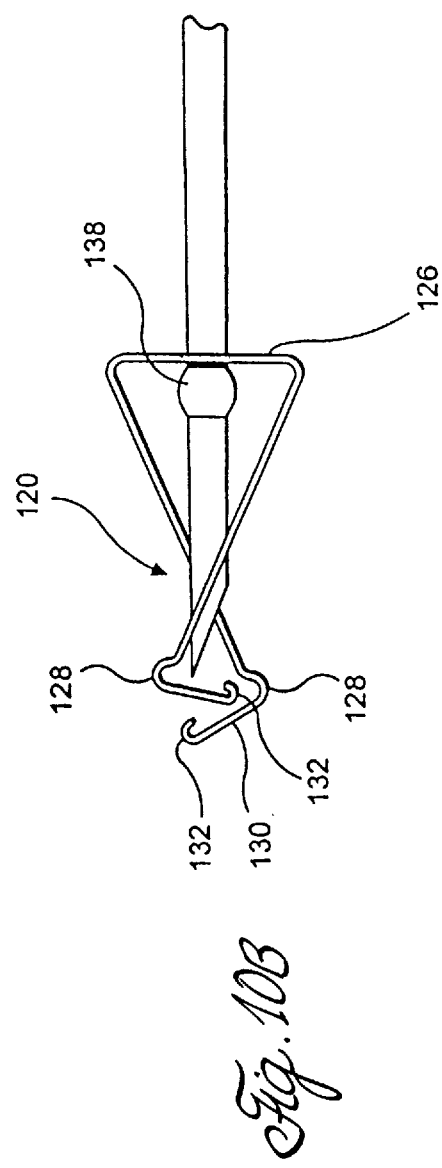

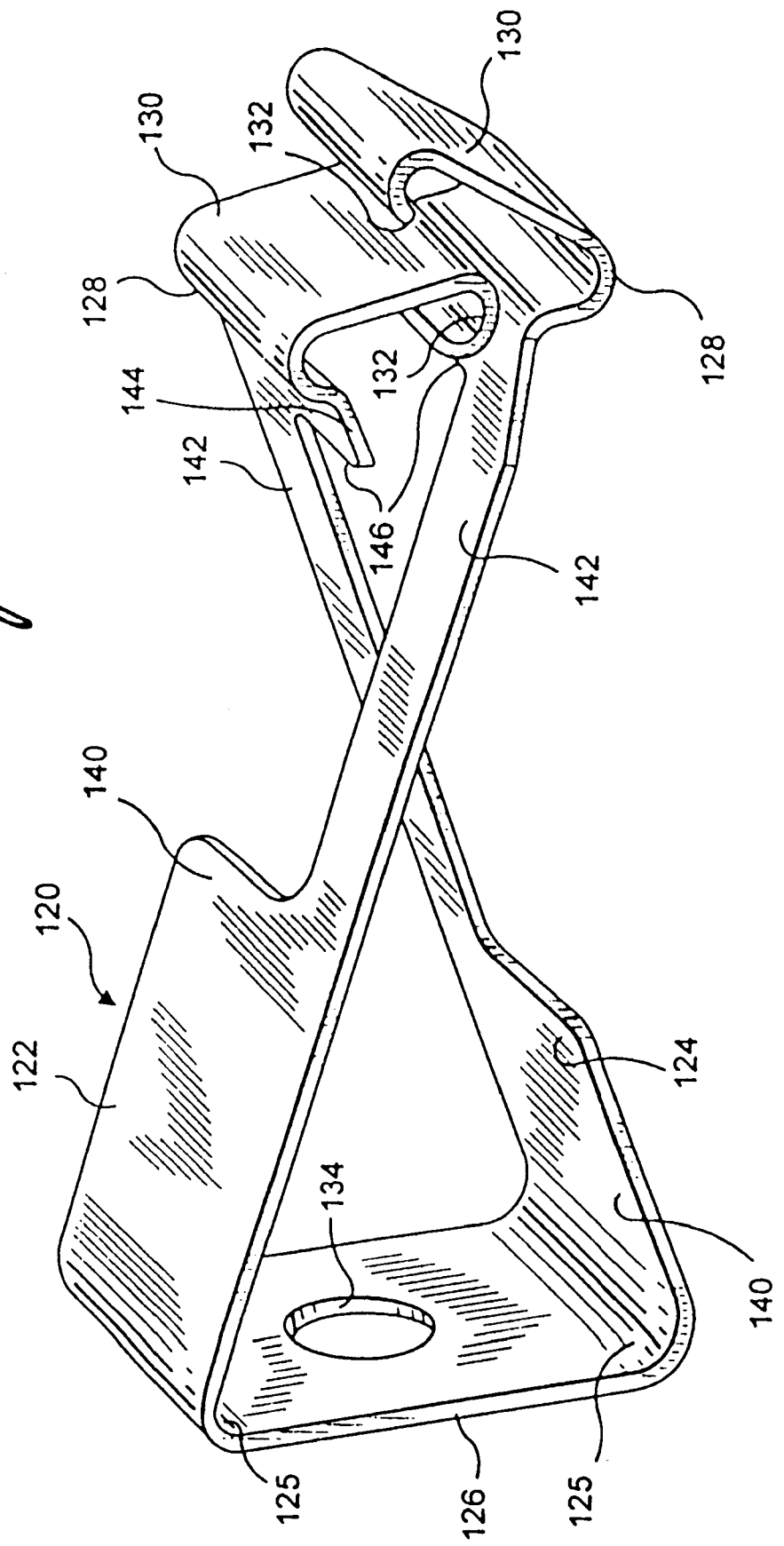

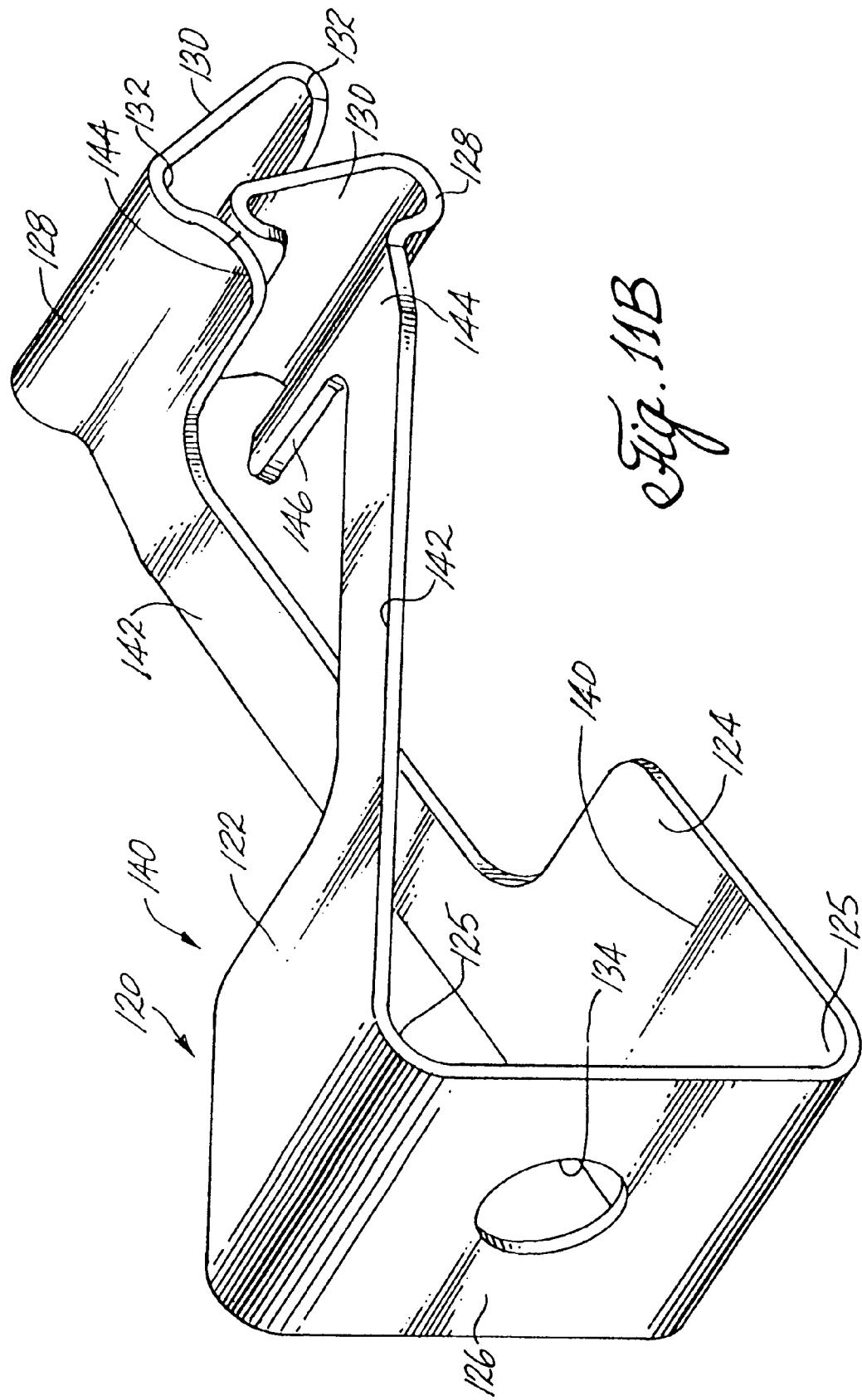

SPRING CLIP SAFETY IV CATHETER

This is a continuation-in-part of application Ser. No. 08/915,148 filed on Aug. 20, 1997 now abandoned.

TECHNICAL FIELD

This invention relates generally to intravenous (IV) catheters, and, in particular, to a safety IV catheter in which the needle tip is automatically covered after needle withdrawal to prevent the health-care worker from making accidental contact with the needle tip.

BACKGROUND OF THE INVENTION

I.V. catheters are primarily used to administer fluids, sometimes containing medications, directly into a patient's vascular system. The catheter is inserted into a patient's vein by a health care worker by using a handheld placement device that includes a sharp tip needle. The needle is positioned in the interior hollow portion of the catheter with its tip extended slightly beyond the edge of the catheter. The end of the apparatus opposite the needle tip is made up of the needle connected to a needle hub which is capable of being held by the health care worker during the insertion procedure.

The insertion procedure contains four basic steps: (1) the health care worker inserts the needle and catheter together into the patient's vein; (2) after insertion into the vein with the needle point, the catheter is forwarded into the vein of the patient by the health care worker pushing the catheter with his or her finger; (3) the health care worker withdraws the needle by grasping the hub end (opposite the point end) while at the same time applying pressure to the patient's skin at the insertion site with his or her free hand; and (4) the health care worker then tapes the now inserted catheter to the patient's skin and connects the exposed end of the catheter, the catheter hub, to the source of the fluid to be administered into the patient's vein.

The problem is that immediately after the withdrawal of the needle from the patient's vein, the health care worker who is, at this time, involved in at least two urgent procedures must place the exposed needle tip at a nearby location and address the tasks required to accomplish the needle withdrawal. It is at this juncture that the exposed needle tip creates a danger of an accidental needle stick occurring, which under the circumstances, leaves the health care worker vulnerable to the transmission of various, dangerous blood-borne pathogens, including AIDS and hepatitis.

This danger to the health care worker from accidental needle sticks has caused an impetus for the development of a safer IV catheter in which the occurrence of such accidental needle sticks is prevented. Safety catheters that have been developed to achieve this result are disclosed, for example, in Lemieux Reissue Patent No. Re. 34,416, Crawford U.S. Pat. No. 5,558,651, McLees U.S. Pat. No. 5,135,504, Gaba U.S. Pat. No. 5,697,907, and Dombrowski U.S. Pat. No. 4,978,344. Kulli U.S. Pat. No. 4,929,241 and Chamuel U.S. Pat. No. 5,053,017 disclose a protective needle guard for use with a hypodermic needle.

The prior art safety catheters all exhibit one or more drawbacks that have thus far limited their usefulness and full acceptance by health-care workers. For example, in the safety catheter disclosed in the Lemieux patent, the force required to engage the needle slot within the guard flange is relatively great and would interfere with the removal of the needle. Reducing this force to a more acceptable level would create the possibility of the needle guard remaining in the catheter hub after the needle is removed from the catheter. As a result, the safety catheter disclosed in the Lemieux patent would not consistently function in a reliable manner.

Similarly, the user of the safety catheter disclosed in the Dombrowski patent would have to exert a considerable force to remove the protective cap from the catheter hub, when the cap engages a needle. The safety catheter disclosed in the Dombrowski patent would also be relatively expensive to fabricate because of its inclusion of a flexible flange and a tether.

The McLees protective device requires an irksome, extra pulling action or tug on the needle guard through a retention ring to remove the protected needle from the catheter hub. The McLees device also requires the assembly of two separate components and is thus relatively costly to manufacture. In addition, the needle in the McLees device includes a larger diameter portion near and at the needle tip. This feature of the McLees device would require that the remainder of the needle be of a lesser diameter which would have the adverse effect of slowing the blood flashback through the needle.

SUMMARY OF THE INVENTION

It is accordingly an object of the present invention to provide a safety IV catheter, which reliably and automatically prevents accidental, inadvertent contact with the needle tip after use.

It is a further object of the invention to provide a safety catheter which provides reliable protection to the health care practitioner against needle sticks without requiring any change in the manner of use of the safety catheter by the practitioner.

It is another object of the present invention to provide a safety IV catheter of the type described which is relatively simple and inexpensive to manufacture.

It is yet a further object of the present invention to provide a safety catheter of the type described in which removal of the needle from the needle guard after use is prevented.

To these ends, the safety IV catheter of the invention includes a resilient spring clip needle guard that includes a distal or front end and a proximal or rear wall. The spring clip is inserted into the catheter hub and is urged by the needle shaft into contact with the inner walls of the catheter hub so that the needle guard is reliably retained therein. When the needle is withdrawn from the catheter, the force it had previously exerted on the needle guard is released causing the needle guard to pivot within the catheter hub until it clamps onto the needle shaft. At this time, the distal end wall of the needle guard blocks the distal pointed end tip of the needle. In addition, the spring clip and protected needle onto which it is clamped can be readily and safely removed from the catheter hub. The needle may be provided with a slot or a bulge which cooperates with the needle guard to prevent the inadvertent removal of the needle from the needle guard after their removal from the catheter hub.

In another embodiment of the spring clip safety catheter of the invention, a retaining groove or bump is formed in the inner wall of the catheter hub, which, in the ready position, engages a lower arm of the spring clip to add in the retention of the spring clip in the catheter hub.

In yet a further embodiment of the spring clip safety catheter of the invention, a slot is formed in the needle. After the spring clip has pivoted to its retracted position and the needle is clamped by the spring clip, further movement of the needle in the proximal direction will cause the rear or proximal arm of the spring clip to seat in the slot, thereby to more securely clamp the needle shaft to the spring clip.

In a further embodiment of the spring clip catheter guard of the invention, a tether is connected to the needle hub and the spring clip guard to prevent the spring clip guard from being pulled off the protected needle without requiring an excessive clamping force therebetween.

In yet a further embodiment of the invention the spring clip needle guard is in the form of resilient intersecting arms, each terminating at a distal guard wall. When the needle is in the ready position it passes through the guard and urges the resilient arms away from each other and against the inner wall of the catheter hub. When the needle is retracted past the guard walls, the resilient arms spring to the safety position in which both of the guard walls are positioned distally from the needle tip, thereby to form a barrier that prevents inadvertent contact with the needle tip.

To the accomplishment of the above and to such further objects as may hereinabove appear, the present invention relates to a safety IV catheter as described with respect to presently preferred embodiments in the following specification, as considered with the accompanying drawings, in which:

BRIEF DESCRIPTION OF THE DRAWINGS

FIGS. 1A and 1B are views in partial cross-section of a safety IV catheter in accordance with a first embodiment of the invention in the ready and retracted positions, respectively;

FIGS. 1C and 1D are views similar to FIGS. 1A and 1B of a possible variation to the embodiment illustrated therein;

FIGS. 2A and 2B are views in partial cross-section of a safety IV catheter in accordance with a second embodiment of the invention in the ready and retracted positions, respectively;

FIGS. 3A and 3B are views in partial cross-section of a safety IV catheter in accordance with a third embodiment of the invention in the ready and retracted positions, respectively;

FIGS. 4A and 4B are views in partial cross-section of a safety IV catheter in accordance with a fourth embodiment of the invention in the ready and retracted positions, respectively;

FIGS. 5A and 5B are views in partial cross-section of a safety IV catheter in accordance with a fifth embodiment of the invention in the ready and retracted positions;

FIGS. 6A and 6B are views in partial cross-section of a safety IV catheter in accordance with a sixth embodiment of the invention in the ready and retracted positions, respectively;

FIGS. 7A, 7B and 7C are views in partial cross section of a safety IV catheter in accordance with a further embodiment of the invention in the ready, engaged and retracted or protected positions, respectively;

FIGS. 7D and 7E are views similar to FIGS. 7A and 7B of a possible variation to the embodiment of the invention illustrated therein;

FIG. 8 is a perspective of the spring clip needle guard used in the embodiment of FIG. 7;

FIG. 9 is a cross-section of the spring clip needle guard of FIG. 8;

FIGS. 10A and 10B are views in partial cross-section of a safety IV catheter in accordance with still a further embodiment of the invention shown in the ready and protected positions, respectively;

FIG. 11A is a perspective of the needle guard clip of the embodiment of FIG. 10; and FIG. 11B is a view similar to FIG. 11A of the needle guard of the embodiment of FIG. 10.

DESCRIPTION OF THE PREFERRED EMBODIMENTS

The safety IV catheter of the invention, generally designated 10, in the embodiment illustrated in FIGS. 1A and 1B, includes a needle hub 12 that includes an axial opening 14 which securely receives the proximal end of a needle 16 having a sharpened tip 18. The needle hub 12, as is conventional, is hollow and includes a flash chamber 22. As is also conventional, the needle 16 is received within a hollow tubular catheter 24, the proximal end of which is concentrically affixed within the distal end of a catheter hub 26 having a distal section 28 and a contiguous, larger diameter proximal section 30.

The catheter hub 26 terminates at its proximal end in a luer fitting 32 adapted to receive a tubing set, which in a known manner, administers intravenous fluid into the patient. The catheter 24 is secured within an axial passageway 34 in distal hub section 28 by means of a sleeve 20 received within passageway 34, which engages the proximal end of the catheter. Passageway 34 communicates at its proximal end with a flash chamber 36 formed in hub section 30.

In the ready position of the catheter shown in FIG. 1A, the distal end of the needle hub 12 is snugly received in the proximal end of the interior of chamber 36 such that the needle 16 extends through the chamber 36, the passageway 34 and distally beyond the catheter hub 26 and catheter 24 so that its tip extends beyond the tapered distal end of the catheter.

In use, the distal tip of the needle and the catheter are inserted into a patient's vein. Thereafter, the health care practitioner manually places the catheter further into the vein and then withdraws the needle by grasping and moving by hand the proximal end of the needle hub 12. The luer of the catheter hub 26 is then fitted with a source of the fluid that is to be administered into the patient's vein.

In accordance with the present invention, as the needle 16 is being withdrawn from the patient, a protective needle guard 40 located within hub chamber 36 automatically snaps into a retracted position in which it blocks access to the distal needle tip and prevents further distal movement of the needle tip, thereby to prevent accidental contact by the health care practitioner with the needle tip.

As shown in FIGS. 1A and 1B, the needle guard 40 is in the form of a unitary spring clip that is preferably made of a resilient metal such as stainless steel. The spring clip includes a distal arm 42 terminating at its upper end in a curved lip 44, and at its lower end in a pointed end 46, which, in the embodiment of FIG. 1, is received within a mating groove 48 formed in the lower interior wall of catheter hub section 30.

The spring clip needle guard 40 further includes a transverse segment 50 that extends upward and proximally from lower pointed end 46 and terminates at a U-shaped upper end 52. In the ready position of the spring clip shown in FIG. 1A, upper end 52 abuts against the upper interior wall of the catheter hub section 30. The spring clip guard 40 further includes a vertical arm 54 that extends downward from the U-shaped upper end 52 and terminates above the lower wall of catheter hub section 30. Transverse segment 50 and proximal vertical arm 54 respectively include axially aligned openings 56, 58 through which the shaft of needle 16 is free to pass and axially move. The diameter of opening 58 is slightly greater than that of the needle shaft, whereas the diameter of the opening 56 is greater than that of opening 58.

In the ready position of the catheter prior to needle withdrawal, the shaft of needle 16 engages the curved lip 44 of the spring clip needle guard 40, thereby to exert an essentially downward force on the resilient spring clip. That force causes the lower end 46 of the spring clip to seat securely in groove 48 at point a. That contact, in addition to the abutment of the upper end 52 of the spring clip with the upper interior wall at the catheter hub at point b, securely maintains the spring clip needle guard 40 in the ready position within the catheter hub.

As the needle 16 is retracted to the left, as viewed in FIG. 1A, to its fully retracted position shown in FIG. 1B, after catheter insertion into the patient's vein, the distal tip of the needle moves proximally past the curved lip 44 of the spring clip needle guard 40 at point c, at which time the downward force previously exerted by the needle shaft on the spring clip is released.

As a result of the needle 16 moving proximally past point c, the retention force on spring clip needle guard 40 in the catheter hub is released causing the spring clip needle guard 40 to pivot or snap in a clockwise direction to the retracted position shown in FIG. 1B. As therein shown, distal arm 42 of the needle guard 40 blocks the distal path of the needle 16. Simultaneously with the blocking and releasing actions, the spring clip guard 40 becomes securely clamped onto the needle shaft at points d and e, thereby to securely lock the needle guard 40 onto the needle shaft. At this time, the needle 16 and needle guard 40 can be removed together from the catheter hub 26, and the tip of the needle cannot be pushed past the needle guard because it is blocked by the distal arm 42 and lip 44 of the needle guard.

If desired, a slot 60 may be formed in the needle shaft slightly proximal to the needle tip. When the needle and needle guard are in their retracted and clamped positions (FIG. 1B), slot 60 is positioned slightly distal to the clamping point e of the transverse segment of the needle guard 40 such that if a subsequent attempt is made to move the needle further in a rearward or proximal direction, the transverse segment 50 at point e will seat into slot 60, thereby to provide an additional force to retain the needle guard 40 on the needle 16 in the protected position in which access to the needle tip is prevented.

The safety IV catheter illustrated in FIGS. 1C and 1D is the same as that illustrated in FIGS. 1A and 1B, except that the slot 60 in the needle shaft in the latter is replaced in the former by a bulge 61 whose diameter is greater than that of opening 58 in vertical arm 54. If an attempt is made to move the protected needle illustrated in FIG. 1C in the rearward or proximal direction, bulge 61 will engage wall 54 and will thus not be able to pass through opening 58, so as to prevent further proximal movement of the needle and removal of the needle from the needle guard, as defined.

The embodiment of the invention illustrated in FIG. 2 is similar to that of FIG. 1 except that instead of the groove formed in the lower wall of the catheter hub that engages the lower end of the spring clip, a retaining bump 62 is formed in that wall against which the lower end 46 of the needle guard 42 seats when the needle guard 40 is in the ready position in FIG. 2A.

The embodiment of the invention illustrated in FIGS. 3A and 3B is essentially the same as that of FIG. 2 with the addition of a tether 64 secured at one end to the needle hub 12 and at its other end to proximal arm 54 of the spring clip needle guard 40. As shown in FIG. 3B, the tether 64 is extended to its full length when the needle hub is retracted to achieve needle removal so as to more securely retain the needle hub 12 and the spring clip needle guard 40 when the latter is clamped onto the needle when in the retracted position, in which, as described above, the distal arm 42 of the spring clip prevents access to the needle tip, and the needle guard 40 and needle are released from the catheter hub.

FIGS. 4A and 4B illustrate a spring clip needle guard embodying the principles of the invention in an alternative configuration. As therein shown, the spring clip needle guard 40a includes a distal arm 65 terminating at its upper end in a curved lip 66, and at its lower end in a U-shaped portion 67 which, in the ready position illustrated in FIG. 4A, contacts a bump 68 formed in the lower inner wall of the catheter hub.

A transverse segment 69 having a central opening 70 extends proximally and upwardly and terminates at an upper U-shaped portion 72. A proximal end wall 74 having an opening 76 depends vertically from portion 72 and then extends distally in a horizontal lower segment 78, which has an opening 80 through which the lower halves of distal arm 65 and transverse segment 69 extend in the ready position of the needle guard. Segment 78 at its distal end extends upwardly at a front wall 82, which has a central opening 84 axially aligned with openings 70, 76. At its upper end, distal front wall 82 extends in the proximal direction in an upper segment 86 which, as shown in FIG. 4A, contacts the upper inner wall of the catheter hub along substantially its entire length.

As shown in FIG. 4A, when the catheter is in the ready position, the needle shaft passes through openings 70, 76 and 84 and rests on curved lip 66, urging arm 65 against bump 68 in the lower wall of the catheter hub. That engagement along with the resilient engagement of upper segment 86 with the upper interior wall of the catheter hub retains the spring clip 40a in its ready position within the catheter hub.

When the needle hub and needle are retracted to the right, as viewed in FIG. 4A, by a sufficient amount, the needle tip passes below lip 66 and then releases its downward force on arm 65. As described above, with reference to the first-described embodiment, this release of engagement of the needle shaft and spring clip arm 65 causes arm 65 to snap upwards to the retracted position illustrated in FIG. 4B, in which arm 65 and lip 66 extend over the needle tip and thereby prevent accidental contact with the needle tip as desired. In this condition, the needle guard is clamped onto the needle shaft in essentially the same manner described above with respect to the first-described embodiment, and the needle and needle guard clamped thereto can be readily removed from the catheter hub, also as described above, and as shown in FIG. 4B.

The embodiment of the needle guard illustrated in FIGS. 5A and 5B is essentially the same as that shown in FIGS. 4A and 4B with the addition of a slot 90 near the distal tip end of the needle. When the needle and needle guard are in their retracted and clamped position (FIG. 5B), slot 90 is positioned slightly distal to the clamping point of the transverse segment 69 such that if a subsequent attempt is made to move the needle further in a rearward or proximal direction, the transverse segment 69 will seat into slot 90, thereby to provide an additional force to retain the needle guard in the needle in the protected position in which access to the needle tip is prevented.

The embodiment of the invention illustrated in FIGS. 6A and 6B is the same as that illustrated in FIGS. 4A and 4B except for the inclusion of a tether 92 secured at one end to the needle hub and at its other end to the proximal wall of the spring clip needle guard. As shown in FIG. 6A, in the ready position, the tether is wound around the distal end of the needle hub. As shown in FIG. 6B, when the needle and needle guard are in their retracted position, the tether is extended to its full length and adds in the retention of the needle guard to the needle hub. If desired, the embodiment of the invention embodiment illustrated in FIGS. 6A and 6B could also include a needle slot as in the embodiment of the invention illustrated in FIGS. 5A and 5B.

The embodiment of FIGS. 7A–C, differs from the previously described embodiments primarily with regard to the construction and operation of the spring clip needle guard 96. As shown in FIGS. 8 and 9, the spring clip 96 includes a central transverse section 98 which includes a central slot 100. A sloping section 102 extends from section 98 in the proximal direction and terminates at a curved end 104 from which a proximal vertical arm 106 extends. Arm 106 terminates at its lower end in a U-shaped section 108. The distal end of transverse section 98 terminates in a curved section 110 from which a vertical proximal arm 112 extends. Distal arm 112 terminates at its upper end in a curved arm 114.

A cutout portion in section 98 defines a flexible flap 116 which terminates at its distal free end in a downwardly sloping locking tab 118. As in the prior embodiments, proximal arm 106 includes an opening 58.

As shown in FIG. 7A, spring clip needle guard 96, when in the ready position illustrated therein, is inserted within catheter hub 26 so as to allow the needle 16 to pass through opening 58 and slot 100. As in the previously described embodiments, the curved end 104 abuts against the inner upper wall of the catheter hub 26 at point b, and curved section 110 seats within the mating groove 48 at point a formed in the lower, inner wall of the catheter hub. In addition, the lower curved section 108 contacts at a point f the lower, inner wall of the catheter hub 26 at a location proximal to point b.

In operation, the needle is initially withdrawn into the catheter hub until it reaches the tab engaged position illustrated in FIGS. 7B, in which as therein shown, the locking tab 118 is received within the needle groove or slot 60. At this point, the spring clip remains in contact with the inner wall of the catheter hub at points a, b and f, while the needle tip 18 engages curved end 114, thereby to urge section 110 into groove 48 at point c. The relative position of point f with respect to point b prevents the needle and clip from being prematurely released from the catheter hub by preventing the distal end of the clip from tipping upwards and the proximal end from slipping downward with the clip in the tab engaged position shown in FIG. 7B.

As the needle is withdrawn further away from the patient, as shown in FIG. 7C, the needle tip passes beyond curved end 114, thereby releasing the downward force that had been previously exerted on curved end 114 by the needle.

This sudden release of the downward force on the spring clip end causes the distal end of the spring clip 96 to pivot upward so that distal end 112 of spring clip 96 moves rapidly to a position in which it prevents or blocks motion of the needle in the distal direction. The spring clip 96 is retained on the needle 16 and will be removed from the catheter hub 26 when the needle is completely removed. Movement of the spring clip 96 from its protecting or retracted position shown in FIG. 7C is further prevented by the insertion of the locking tab 118 into the needle groove 60, which prevents the spring clip from rotating around the periphery of the needle. This, in turn, secures the spring clip on the needle even if the clip were subjected to a twisting and pulling force.

The safety IV catheter illustrated in FIGS. 7D and 7E is the same as that illustrated in FIGS. 7A and 7B, except that the slot 60 in the needle shaft in the latter is replaced in the former by a bulge 61 whose diameter is greater than that of opening 58 in vertical arm 54. If an attempt is made to move the protected needle illustrated in FIG. 7D in the rearward or proximal direction, bulge 61 will engage wall 54 and will not be able to pass through opening 58, so as to prevent any further proximal movement of the needle and removal of the needle from the needle guard, as desired.

The embodiment of the spring clip needle guard 120 disclosed in FIGS. 10A, 10B, and 11A and 11B comprises first and second arms 122 and 124 respectively joined at their proximal ends in a hinged arrangement at 125 to the ends of a rear wall 126. The distal ends of arms 122, 124 each include a curved protrusion 128 extending to a distal end wall 130, which in turn terminates in a lip 132. As seen best in FIG. 11, rear wall 126 includes a central opening 134, and arms 122 and 124 each include a narrow portion 142 that extends between a proximal wide portion 140 and a distal wide portion 144. A lateral clamping edge 146 is defined at the distal wide portion 144.

As shown in FIG. 10A, when the needle guard 120 is in its ready position, the curved protrusions 128 in each of arms 122, 124 are received in an annular groove or ring 136 formed in the inner wall of catheter hub 26, which, as in the prior embodiments, is removably fit into the distal end of a needle hub 12. Also as in the prior embodiment, a needle 16 having a sharpened tip 18 at its distal end is received within a tubular catheter 24, which is secured to the distal end of catheter hub 26. The proximal end of needle 16 passes through opening 134 in rear wall 126. Needle 16 includes an increased diameter bulge 138, which is sufficiently small to allow needle 16 to move axially along catheter 24, but greater in diameter than opening 134 for reasons to be described below.

In the ready position illustrated in FIG. 10A, the needle shaft passes through the needle guard and applies an outward radial force on resilient arms 122, 124 by means of its engagement with lips 132, so as to urge the curved protrusions 128 of each of the arms into the annular groove 136, so as to retain needle guard 120 in a fixed position within the inner wall of catheter hub 26. The shaft of needle 16 that passes through the needle guard 120 frictionally engages the inner edges of the narrow portions 142 of arms 122, 124 so as to further retain the needle in its ready position.

When the needle is retracted axially within the catheter hub, and moves past the end lips 132 of the needle guard, the radial force previously exerted on arms 122, 124 of needle guard 120 is suddenly released. This causes the distal end walls 130 of the needle guard to be released from their seat in the annular groove 136 and to pivot inwards into the catheter hub until, as seen in FIG. 10B, the end walls 130 overlap one another at a location distally in front of the needle tip, thereby to form a barrier that prevents inadvertent contact with the needle tip. At the same time, the clamping edges 146 of the needle guard (FIG. 11B) are urged against the needle tip to restrict further axial movement of the needle.

As also shown in FIG. 10B, the needle guard 120 and the needle clamped to the needle guard after needle retraction can be removed from the catheter hub as a unitary assembly, and safely discarded. If an attempt is made, intentionally or inadvertently, to pull the needle further to the right, as viewed in FIG. 10B, out of the needle guard, the bulge 138 on the needle shaft will come into contact with the end wall 126, and since its diameter is greater than that of opening 134, the end wall 126 will at this point prevent any further axial movement of the needle out of the needle guard.

It will thus be appreciated that the spring clip needle guard of the invention as employed in an IV catheter provides automatic and reliable protection of the needle tip upon needle retraction to prevent accidental contact with the needle tip by a health care practitioner. It will also be appreciated that modifications may be made to the embodiments of the invention specifically described hereinabove without necessarily departing from the spirit and scope of the invention.

What is claimed is:

1. An IV catheter apparatus comprising a tubular catheter having a proximal end and a distal end, a needle having a needle shaft and a tip, said needle being received within said tubular catheter when in a ready position, a catheter hub attached to the proximal end of said catheter, said catheter hub having a hollow interior and an inner wall, said needle being movable between said ready position in which said tip is outside of said catheter hub and a retracted position in which said tip is within the interior of said catheter hub, a unitary needle guard substantially positioned in the interior of said catheter hub and including a resilient portion engaged by said needle shaft when said needle is in said ready position, a section of said resilient portion of said needle guard being urged by said needle shaft into retaining contact with an interior wall of said catheter hub when said needle is in its said ready position, means formed on said interior wall of said catheter hub for engaging a segment of said needle guard for retaining said needle guard to said catheter hub during the movement of said needle between its said ready position and said retracted position, said needle guard also including a distal wall extending from said resilient portion and spaced from said needle tip when said needle is in its said ready position and movable within the interior of said catheter hub to a blocking position distal of said needle tip when said needle is in its said retracted position in which said needle shaft no longer exerts a force on said resilient portion of said needle guard such that said retaining contact between said section of said needle guard and said catheter hub is released, and means included in said needle guard for clamping said needle guard to said needle upon the movement of said needle guard to its said blocking position.

2. The catheter of claim 1, in which said distal wall of said needle guard is contiguous with said resilient portion, said distal wall including a curved lip engaging the underside of said needle shaft when said needle is in its said ready position.

3. The catheter of claim 2, in which said engaging and retaining means includes a groove formed in said inner wall of said catheter hub, said groove receiving a portion of said needle guard when said needle is in its said ready position.

4. The catheter of claim 1, in which said engaging and retaining means includes a groove formed in said inner wall of said catheter hub, said groove receiving a portion of said needle guard when said needle is in its said ready position.

5. The catheter of claim 1, in which said needle guard further includes a transverse arm and a curved upper segment contiguous with said transverse arm and in contact with an opposed interior wall of the catheter hub when said needle is in its said ready position.

6. The catheter of claim 1, in which said needle guard further comprises a proximal wall having a lower curved segment in contact with said interior wall of said catheter hub when said needle is in its said ready position.

7. The catheter of claim 6, in which said proximal wall further includes an upper end in engagement with an opposed location of said interior wall of said catheter hub when said needle guard is in its said ready position.

8. The catheter of claim 7, in which said engaging and retaining means includes a groove formed in said interior wall of said catheter hub, said distal wall of said needle guard including a lower curved portion seated in said groove when said needle is in its said ready position.

9. The catheter of claim 1, in which said needle guard includes first and second distal walls which overlap one another and form a distal barrier to said needle when said needle guard is in its said blocking position.

10. The catheter of claim 9, in which each of said distal walls includes a curved lip engaging opposing surfaces of said needle shaft when said needle is in its said ready position.

11. The catheter of claim 10, in which said first and second distal walls each include a curved protruding segment, said engaging and retaining means including an annular groove formed in said catheter hub interior wall for receiving said protruding segments when said needle is in its said ready position.

12. The catheter of claim 11, in which said needle guard further comprises a proximal end wall and said first and second distal walls each further include a wide section and a narrow section extending from said wide section toward said proximal end wall.

13. The catheter of claim 12, in which a clamping edge is formed on a proximal edge of each of said wide sections.

14. The catheter of claim 9, in which said needle guard further comprises a proximal end wall having an opening for receiving said needle therethrough and first and second arms extending respectively between said proximal end wall and said first and second distal walls.

15. The catheter of claim 14, in which said needle includes a large diameter segment on the needle shaft inward of said needle tip, the diameter of said large diameter segment being greater than that of said opening in said proximal end wall.

16. The catheter of claim 9, in which said engaging and first and second distal walls each include a curved protruding segment, said retaining means including an annular groove formed in said catheter hub interior wall for receiving said protruding segments when said needle is in its said ready position.

17. The catheter of claim 16, in which said needle guard further comprises a proximal end wall and said first and second distal walls each further include a wide section and a narrow section extending from said wide section toward said proximal end wall.

18. The catheter of claim 17, in which a clamping edge is formed on a proximal edge of each of said wide sections.

19. An IV catheter apparatus comprising a tubular catheter having a proximal end and a distal end, a needle having a needle shaft and a tip, said needle being received within said tubular catheter when in a ready position, a catheter hub attached to the proximal end of said catheter, said catheter hub having a hollow interior and an inner wall, said needle being movable between said ready position in which said tip is outside of said catheter hub and a retracted position in which said tip is within the interior of said catheter hub, and a unitary needle guard substantially positioned in the interior of said catheter hub and including a resilient portion engaged by said needle shaft when said needle is in said ready position, a section of said resilient portion of said needle guard being urged by said needle shaft into retaining contact with an interior wall of said catheter hub when said needle is in its said ready position, said needle guard also including a distal wall extending from said resilient portion and spaced from said needle tip when said needle is in its said ready position and movable within the interior of said catheter hub to a blocking position distal of said needle tip when said needle is in its said retracted position in which said needle shaft no longer exerts a force on said resilient portion of said needle guard such that said retaining contact between said section of said needle guard and said catheter hub is released upon the movement of said needle guard to its said blocking position, said distal wall of said needle guard further including at least one edge extending transversely to the axis of said needle for engaging said needle shaft, thereby to clamp said needle guard to said needle during the movement of said needle guard from its said ready position to its said blocking position.

20. The catheter of claim 19, in which said needle guard includes first and second distal walls which overlap one another and form a distal barrier to said needle when said needle guard is in its blocking position.

21. The catheter of claim 20, in which first and second clamping edges are formed respectively in said first and second distal walls and engage opposing surfaces of said needle when said needle guard is in its said blocking position.

22. The catheter of claim 21, in which said needle guard further comprises a proximal end wall having an opening for receiving said needle therethrough and first and second arms extending respectively between said proximal end wall and said first and second distal walls.

23. The catheter of claim 22, in which said first and second distal walls include a wide section and a narrow section extending from said wide section toward said proximal end wall.

24. The catheter of claim 23, in which said first and second clamping edges are respectively is formed on a proximal edge of each of said wide sections.

25. The catheter of claim 22, in which said needle includes a large diameter segment on the needle shaft inward of said needle tip, the diameter of said large diameter.

* * * * *

UNITED STATES PATENT AND TRADEMARK OFFICE
CERTIFICATE OF CORRECTION

PATENT NO. : 6,117,108
DATED : September 12, 2000
INVENTOR(S) : Kevin Woehr, Manfred Orth, Mark Wynkoop and Matthew Kohler It is certified that error appears in the above-identified patent and that said Letters Patent is hereby corrected as shown below:

Title page:
Replace "[76] Inventors." with -- [75] Inventers: --
Insert -- [73] Assignee: B. Braun Melsungen AG, Melsungen AG,
Melsungen, Germany --

In the Drawings
Replace FIGS. 3B, 5A, 5B, 7A, 7B, 7C, 8, 9, 7D, 7E with the following:

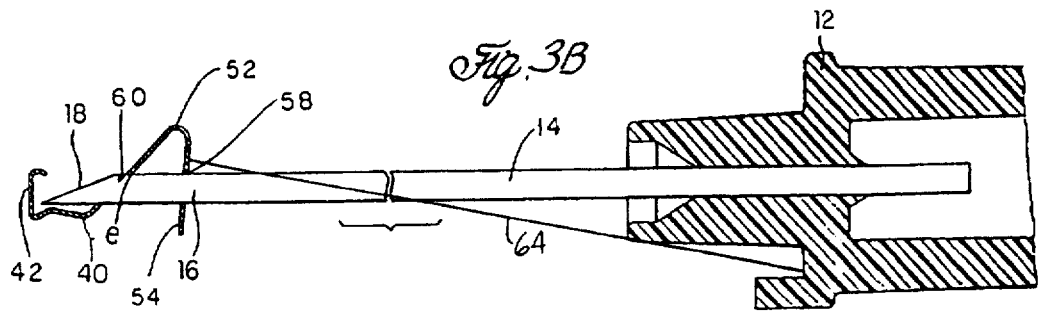

UNITED STATES PATENT AND TRADEMARK OFFICE
CERTIFICATE OF CORRECTION

PATENT NO. : 6,117,108
DATED : September 12, 2000
INVENTOR(S) : Kevin Woehr, Manfred Orth, Mark Wynkoop and Matthew Kohler It is certified that error appears in the above-identified patent and that said Letters Patent is hereby corrected as shown below:

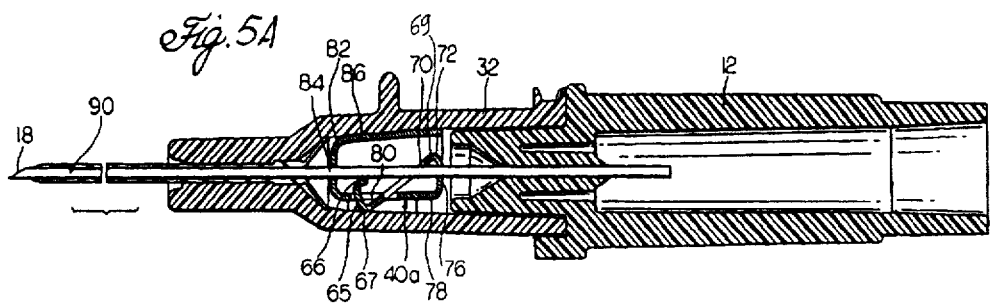

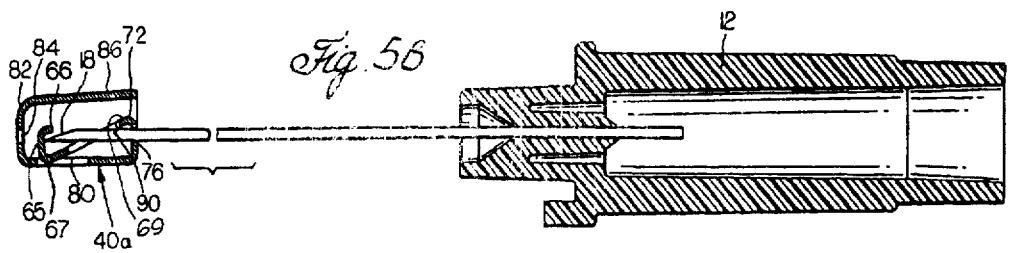

UNITED STATES PATENT AND TRADEMARK OFFICE
CERTIFICATE OF CORRECTION

PATENT NO. : 6,117,108                                              Page 3 of 7
DATED     : September 12, 2000
INVENTOR(S) : Kevin Woehr, Manfred Orth, Mark Wynkoop and Matthew Kohler It is certified that error appears in the above-identified patent and that said Letters Patent is hereby corrected as shown below:

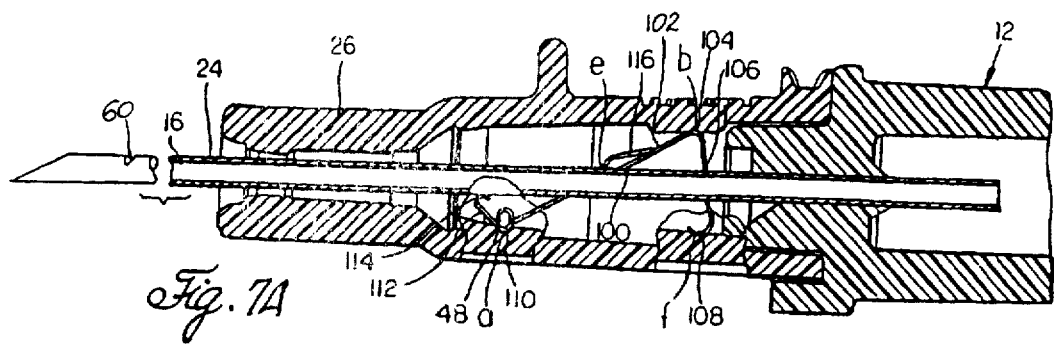

Fig. 7A

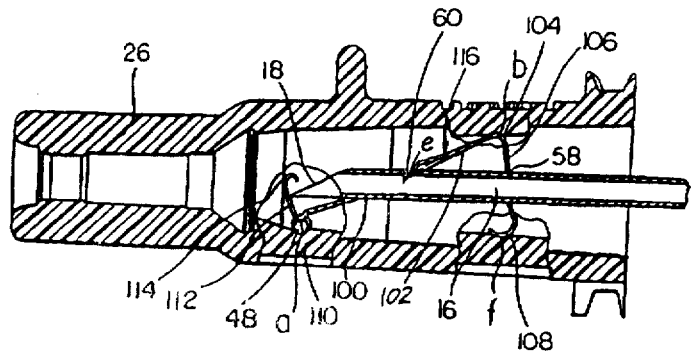

Fig. 7B

UNITED STATES PATENT AND TRADEMARK OFFICE
CERTIFICATE OF CORRECTION

PATENT NO. : 6,117,108
DATED : September 12, 2000
INVENTOR(S) : Kevin Woehr, Manfred Orth, Mark Wynkoop and Matthew Kohler It is certified that error appears in the above-identified patent and that said Letters Patent is hereby corrected as shown below:

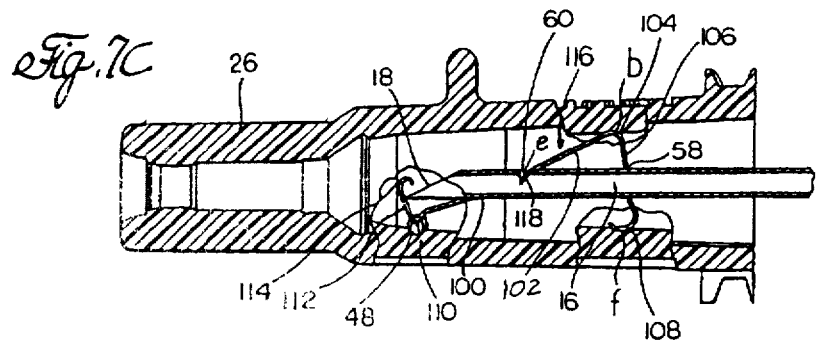
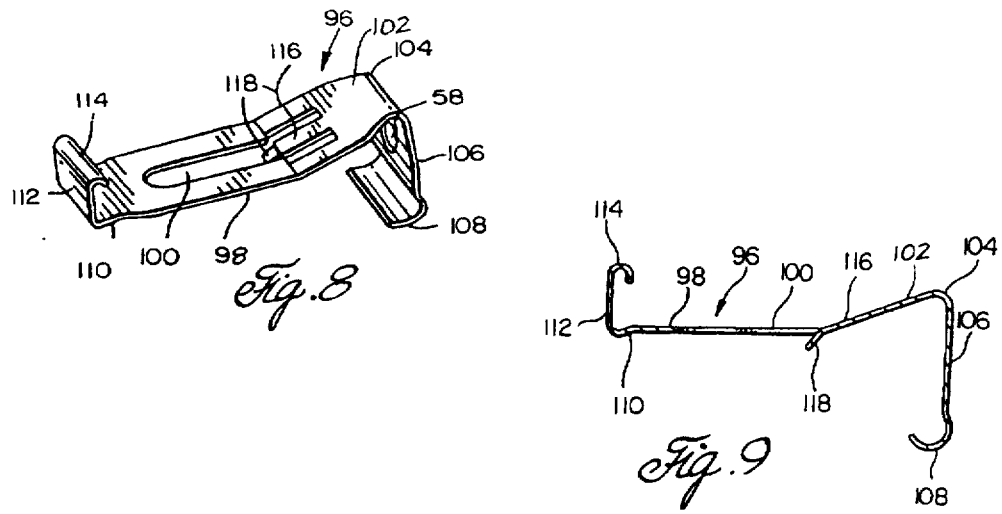
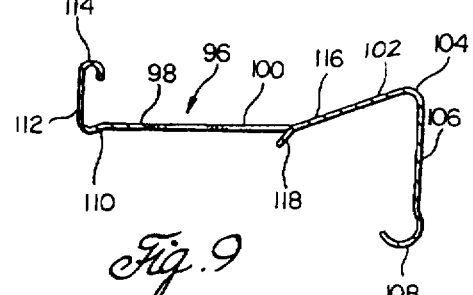

UNITED STATES PATENT AND TRADEMARK OFFICE
CERTIFICATE OF CORRECTION

PATENT NO. : 6,117,108
DATED : September 12, 2000
INVENTOR(S) : Kevin Woehr, Manfred Orth, Mark Wynkoop and Matthew Kohler Page 5 of 7

It is certified that error appears in the above-identified patent and that said Letters Patent is hereby corrected as shown below:

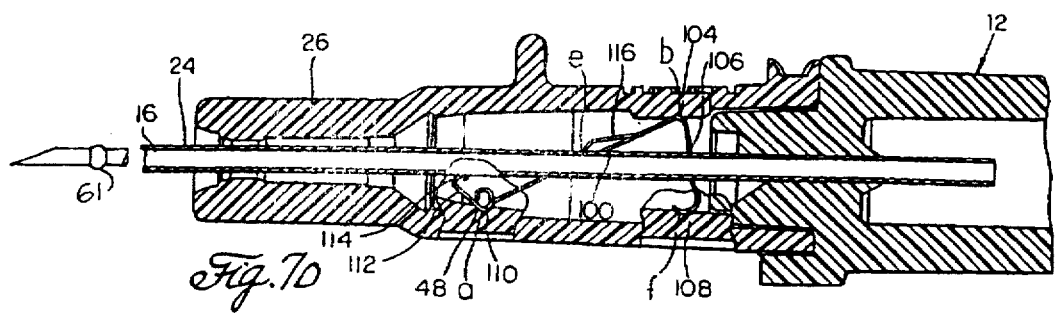

Fig. 7D

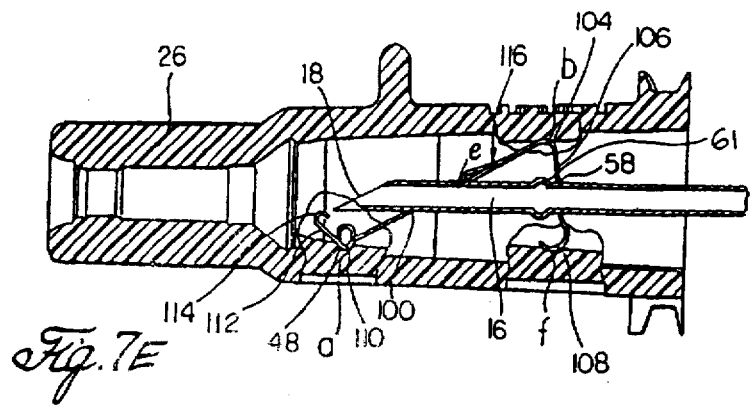

Fig. 7E

UNITED STATES PATENT AND TRADEMARK OFFICE
CERTIFICATE OF CORRECTION

PATENT NO. : 6,117,108
DATED : September 12, 2000
INVENTOR(S) : Kevin Woehr, Manfred Orth, Mark Wynkoop and Matthew Kohler It is certified that error appears in the above-identified patent and that said Letters Patent is hereby corrected as shown below:

Column 5,
Line 15, replace "retracted to the left" with -- retracted to the right --.

Column 7,
Line 11, after "invention" delete "embodiment".
line 24, replace "proximal arm 112" with -- distal arm 112 --.
line 45, replace "FIGS. 7B" with -- FIG. 7B --."
line 50, replace "at point c" with -- at point a -- ;

Column 8,
Line 10, after "bulge 61" insert -- (FIG. 7E) --.
Line 18, replace "FIGS. 10A, 10B, and 11A and 11B" with -- FIGS. 10A, 10B, 11A and 11B --.

Column 10,
Line 45, after "which said" delete "engaging and".
Line 47, after "segment, said" insert -- engaging and --.

Column 12,
Lines 8-19, replace claims 22, 23 and 24 with the following:
-- 22. The catheter of claim 21 in which said first and second distal walls include a wide section and a narrow section extending from said wide section toward said proximal end wall.--

-- 23. The catheter of claim 22 in which said first and second clamping edges are respectively formed on a proximal edge of each of said wide sections.

UNITED STATES PATENT AND TRADEMARK OFFICE
CERTIFICATE OF CORRECTION

PATENT NO. : 6,117,108
DATED : September 12, 2000
INVENTOR(S) : Kevin Woehr, Manfred Orth, mark Wynkoop and Matthew Kohler It is certified that error appears in the above-identified patent and that said Letters Patent is hereby corrected as shown below:

-- 24. The catheter of claim 23 in which said needle guard further comprises a proximal end wall having an opening for receiving said needle therethrough and first and second arms extending respectively between said proximal end wall and said first and second distal walls. --.

Line 22, after "large diameter" insert --segment being greater than that of said opening in said proximal end wall --.

Signed and Sealed this

Twenty-eighth Day of August, 2001

*Attest:*

*Attesting Officer*

NICHOLAS P. GODICI
*Acting Director of the United States Patent and Trademark Office*